United States Patent [19]

Randell et al.

[11] B  4,014,887

[45] Mar. 29, 1977

[54] SUBSTITUTED PIPERIDIN-4-OLS

[75] Inventors: Donald Richard Randell, Stockport; Brian Holt, Royton; Alan Geoffrey Virgin, Swinton, all of England

[73] Assignee: Ciba-Geigy Corporation, Ardsley, N.Y.

[22] Filed: Oct. 19, 1973

[21] Appl. No.: 408,123

[44] Published under the second Trial Voluntary Protest Program on April 13, 1976 as document No. B 408,123.

[30] Foreign Application Priority Data

Oct. 21, 1972 United Kingdom ............ 48601/72

[52] U.S. Cl. .................. 260/293.84; 260/45.8 N; 260/293.63; 260/293.64; 260/293.66; 260/293.67; 260/293.88; 260/293.89; 260/293.9

[51] Int. Cl.$^2$ ....................... C07D 211/46

[58] Field of Search ............. 260/293.63, 293.64, 260/293.66, 293.67, 293.84, 293.88, 293.89, 293.9

[56] References Cited

UNITED STATES PATENTS

| | | | |
|---|---|---|---|
| 3,120,540 | 2/1964 | Meltzer et al. | 260/294.3 |
| 3,534,048 | 10/1970 | Murayama et al. | 260/293 |
| 3,733,326 | 5/1973 | Murayama et al. | 260/290 V |
| 3,759,926 | 9/1973 | Chalmers et al. | 260/293.9 |

FOREIGN PATENTS OR APPLICATIONS 2,040,983   3/1971   Germany

OTHER PUBLICATIONS

Fankhauser et al., Helv. Chim. Acta 49 (1), pp. 690–695 (1966); Chem. Abstracts 64: 14163d.

*Primary Examiner*—G. Thomas Todd
*Attorney, Agent, or Firm*—Nestor W. Shust

[57] ABSTRACT

Disclosed are stabilized compositions comprising a polymer, especially polyolefines, and a minor proportion of a 1,2,2,6,6-pentasubstituted piperidin-4-ol. The new compositions possess good light stability.

7 Claims, No Drawings

SUBSTITUTED PIPERIDIN-4-OLS

The present invention relates to compounds useful as stabilisers and in particular to 1,2,2,6,6-penta-substituted piperidin-4-ols, some of which are new compounds, useful as stabilisers for polymers.

According to the present invention, there is provided a composition comprising an organic material and, as stabiliser, a compound having the formula:

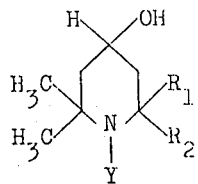

wherein $R_1$ and $R_2$ are the same or different and each is a straight- or branched alkyl residue having from 1 to 12 carbon atoms, or $R_1$ and $R_2$, together with the carbon atom to which they are attached, form a cycloalkyl residue having from 5 to 12 carbon atoms or the group:

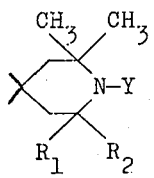

wherein $R_1$ and $R_2$ have their previous significance and Y is a straight- or branched alkyl residue having from 1 to 20 carbon atoms, an alkenyl or alkynyl residue having from 3 to 20 carbon atoms, an aralkyl residue having from 7 to 12 carbon atoms or the group —CH$_2$X wherein X is the group

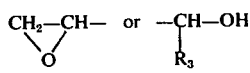

wherein $R_3$ is hydrogen, a methyl or phenyl residue, the group

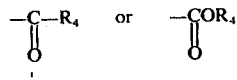

wherein $R_4$ is an alkyl residue having from 1 to 20 carbon atoms.

Examples of the substituents $R_1$ and $R_2$ are methyl, ethyl, n-propyl, isopropyl, n-butyl, sec-butyl, n-hexyl, n-octyl and n-dodecyl residues, and when $R_1$ and $R_2$, together with the carbon atom to which they are attached, form a cycloalkyl residue, examples of such residues are those having the formula:

  

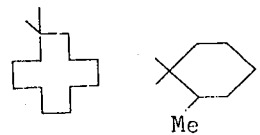

Particularly preferred substituents $R_1$ and $R_2$ are straight or branched alkyl groups having 1 to 4 carbon atoms and the most preferred substituents $R_1$ and $R_2$ are methyl residues.

When Y is an alkyl residue, it may be for instance a methyl, ethyl, n-propyl, isopropyl, n-butyl, sec-butyl, n-hexyl, n-octyl, n-dodecyl, n-octadecyl, or eicosyl residue. Preferred alkyl groups Y are those having from 1 to 4 carbon atoms, the methyl residue being particularly preferred.

Examples of alkenyl residues Y include 10-undecenyl and oleyl, and, more preferably, allyl and α-methallyl groups.

The preferred alkynyl residues Y are those containing 3 or 4 carbon atoms, in particular the propargyl group.

Preferred examples of aralkyl residues Y are those containing from 7 to 11 carbon atoms for instance benzyl, α-methylbenzyl, p-methylα-methylbenzyl and α-naphthylmethyl groups.

Examples of residues —CH$_2$X include 2-hydroxyethyl, 2-hydroxy-2-phenylethyl and 2,3-epoxy-n-propyl groups; 2-hydroxy ethyl and 2-hydroxypropyl groups being preferred.

When the substituent Y has the formula

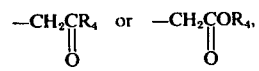

examples of such substituents include methylcarbonylmethyl, n-butylcarbonylmethyl, n-dodecylcarbonylmethyl, eicosylcarbonylmethyl, methoxycarbonylmethyl, ethoxycarbonylmethyl, n-decyloxycarbonylmethyl and n-octadecyloxycarbonylmethyl groups.

Examples of the compounds of formula I useful according to the invention are given in the following list:

1-methyl-2,2,6,6-tetramethylpiperidin-4-ol
1-ethyl-2,2,6,6-tetramethylpiperidin-4-ol
1-n-propyl-2,2,6,6-tetramethylpiperidin-4-ol
1-isopropyl-2,2,6,6-tetramethylpiperidin-4-ol
1-n-butyl-2,2,6,6-tetramethylpiperidin-4-ol
1-secbutyl-2,2,6,6-tetramethylpiperidin-4-ol
1-n-hexyl-2,2,6,6-tetramethylpiperidin-4-ol
1-n-octyl-2,2,6,6-tetramethylpiperidin-4-ol
1-n-dodecyl-2,2,6,6-tetramethylpiperidin-4-ol
1-eicosyl-2,2,6,6-tetramethylpiperidin-4-ol
1-allyl-2,2,6,6-tetramethylpiperidin-4-ol
1-α-methallyl-2,2,6,6-tetramethylpiperidin-4-ol
1-(10'-undecenyl)-2,2,6,6-tetramethylpiperidin-4-ol
1-oleyl-2,2,6,6-tetramethylpiperidin-4-ol
1-propargyl-2,2,6,6-tetramethylpiperidin-4-ol
1-benzyl-2,2,6,6-tetramethylpiperidin-4-ol
1-(α-methylbenzyl)-2,2,6,6-tetramethylpiperidin-4-ol)
1-(p-methylbenzyl)-2,2,6,6-tetramethylpiperidin-4-ol
1-α-naphthylmethyl-2,2,6,6-tetramethylpiperidin-4-ol
1-(2'-hydroxyethyl)-2,2,6,6-tetramethylpiperidin-4-ol
1-(2'-hydroxypropyl)-2,2,6,6-tetramethylpiperidin-4-ol
1(2',3'-epoxy-n-propyl)-2,2,6,6-tetramethylpiperidin-4-ol 1-(2'-hydroxy-2'-phenylethyl)-2,2,6,6-tetramethyl-piperidin-4-ol
1-(methylcarbonylmethyl)-2,2,6,6-tetramethylpiperidin-4-ol
1-(n-dodecylcarbonylmethyl)-2,2,6,6-tetramethyl-piperidin-4-ol
1-(eicosylcarbonylmethyl)-2,2,6,6-tetramethylpiperidin-4-ol
1-(methoxycarbonylmethyl)-2,2,6,6-tetramethyl-piperidin-4-ol
1-ethoxycarbonylmethyl)-2,2,6,6-tetramethylpiperidin-4-ol
1-(octadecyloxycarbonylmethyl)-2,2,6,6-tetramethyl-piperidin-4-ol
1-methyl-2,2,-dimethyl-6,6-diethylpiperidin-4-ol
1-methyl-2,2,2-trimethyl-6-isopropylpiperidin-4-ol
1-methyl-2,2-dimethyl-6,6-di-n-dodecylpiperidin-4-ol
1-aza-1,2,2-trimethylspiro-[5,5]-undecan-4-ol
1-n-butyl-2,2-dimethyl-6,6-diethylpiperidin-4-ol
1-aza-1-allyl-2,2-dimethylspiro[5,5]-undecan-4-ol
1-aza-1-benzyl-2,2-dimethylspiro[5,5]-undecan-4-ol.

Compounds of formula I have been found to impart to polyolefines an exceptionally high degree of stability towards deterioration normally induced by the effects of ultra-violet radiation or exposure to heat. Moreover, this improved stability is achieved without affecting the colour properties of the treated polyolefine. The stabilisers of the invention provide effective light and/or heat stabilisation, especially for low- and high-density polyethylene and polypropylene and polystyrene as well as polymers of butene-1, pentene-1, 3-methylbutene-1, hexene-1, 4-methylpentene-1, 4-methylhexene-1 and 4,4-dimethyl-pentene-1, and also co- and terpolymers of olefines, particularly of ethylene or propylene.

Other organic materials susceptible to degradation by the effects of light and the properties of which are improved by the incorporation therein of a compound of Formula I include natural and synthetic polymeric materials, for instance natural and synthetic rubbers, the latter including, for example, homo-, co- and terpolymers of acrylonitrile, butadiene and styrene.

Specific synthetic polymers include polyvinyl chloride and vinyl chloride co-polymers, polyvinyl acetate as well as condensation polymers derived from ether, ester (derived from carboxylic, sulphonic or carbonic acids) amide or urethane compounds; polyvinyl acetals; polyacrylates such as polymers and copolymers of methyl acrylate, ethyl acrylate, methyl methacrylate and ethyl methacrylate; polyamides; urea-formaldehyde and melamine-formaldehyde resins; cellulose plastics such as cellulose acetate, cellulose butyrate and cellulose nitrate. Certain of these polymers can, for instance, form the basis of surface coating media such as paints and lacquers having an oil or resin base, such as an alkyd or polyamide resin.

The amount of the compound of formula I which is incorporated into the organic material in order to achieve maximal protection against degradation by light varies according to the properties of the organic material treated and according to the severity of the light radiation and to the length of exposure. However, for most purposes it is sufficient to use an amount of the compound of formula I within the range of from 0.01% to 5% by weight, more preferably within the range of from 0.1% to 2% by weight based on the weight of untreated organic material.

The compounds of formula I may be incorporated into the polymeric material by any of the known techniques for compounding additives with a polymer. For example, the compound of formula I and the polymer may be compounded in an internal mixer. Alternatively, the compound of formula I may be added as a solution or slurry in a suitable solvent or dispersant, for instance an inert organic solvent such as methanol, ethanol or acetone to powdered polymer and the whole mixed intimately in a mixer, and the solvent subsequently removed. As a further alternative the compound of formula I may be added to the polymer during the preparation of the latter, for instance at the latex stage of polymer production, to provide pre-stabilised polymer material.

Optionally, the composition of the invention may contain further additives, especially those used in polymer formulations, such as antioxidants of the phenol or amine type, U.V. absorbers and light protectants, phosphite stabilisers, peroxide decomposers, polyamide stabilisers, basic co-stabilisers, polyvinyl chloride stabilisers, nucleation agents, plasticizers, lubricants, emulsifiers, anti-static agents, flame-protectants, pigments, carbon black, asbestos, glass fibres, kaolin and talc.

The present invention therefore includes binary, tertiary and multi-component compositions containing the stabiliser of formula I together with one or more functional addditives for polymers.

Examples of suitable antioxidants are those of the hindered phenol type such as those selected from the following groups:

1. Phenolic compounds having the general formula

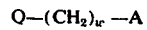

wherein
Q is

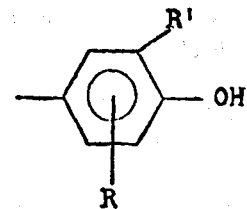

A is — CR(COOR'')$_2$

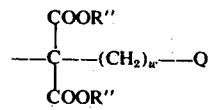

R is hydrogen or lower alkyl
R' is lower alkyl
R'' is alkyl group having from 6–24 carbon atoms
w is an integer from 0 to 4.

Illustrative examples of the compounds shown above are di-n-octadecyl α-(3,5-di-t-butyl-4-hydroxybenzyl)malonate
di-n-octadecyl α-(3-t-butyl-4-hydroxy-5-methyl-benzyl) malonate di-n-octadecyl-α,α'bis-(3-t-butyl-4-hydroxy-5-methylbenzyl) malonate 2. Phenolic compounds having the general formula

Q—R

Illustrative examples of the compounds shown above are 2,6-di-t-butyl-p-cresol
2-methyl-4,6-di-t-butylphenol and the like.
2,6-di-Octadecyl-p-cresol 3. Phenolic compounds having the formula Q—C$_x$H$_{2x}$—Q Illustrative examples of the compounds shown are:

2,2'-methylene-bis(6-t-butyl-4-methylphenol)
2,2'-methylene-bis(6-t-butyl-4-ethylphenol)
4,4'-butylidene-bis(2,6-di-t-butylphenol)
4,4'-(2-butylidene)-bis(2-t-butyl-5-methylphenol)
2,2'-methylene-bis[6-(2-t-methylcyclohexyl)-4-methylphenol]
2,2'-methylene-bis(3-t-butyl-5-ethylphenol)
4,4'-methylene-bis(3,5-di-t-butylphenol)
4,4'-methylene-bis(3-t-butyl-5-methylphenol)
2,2'-methylene-bis(3-t-butyl-5-methylphenol) and the like.

4. Phenolic compounds having the formula

R—O—Q

Illustrative examples of such compounds are 2,5-di-t-butylhydroquinone
2,6-di-t-butylhydroquinone
2,5-di-t-butyl-4-hydroxyanisole 5. Phenolic compounds having the formula

Q—S—Q

Illustrative examples of such compounds are 4,4'-thiobis-(2-t-butyl-5-methylphenol)
4,4'-thiobis-(2-t-butyl-6-methylphenol)
2,2'-thiobis-(6-t-butyl-4-methylphenol)
4,4'-thiobis-(2-methyl-5-t-butylphenol)

6. Phenolic compounds having the formula

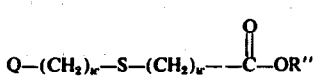

Illustrative examples of such compounds are octadecyl-(3,5-dimethyl-4-hydroxybenzylthio)-acetate
dodecyl-(3,5-di-t-butyl-4-hydroxybenzylthio)-propionate 7. Phenolic compounds having the formula

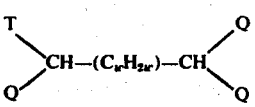

wherein
T is hydrogen
R or Q as defined above.

Illustrative examples of such compounds are 1,1,3-tris(3,5-dimethyl-4-hydroxyphenyl)-propane
1,1,3-tris(5-t-butyl-4-hydroxy-2-methylphenyl)-butane
1,1,5,5-tetrakis(3'-t-butyl-4'-hydroxy-6'-methylphenyl)-n-pentane 8. Phenolic compounds having the formula

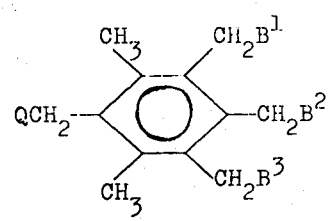

wherein B$^1$, B$^2$ and B$_3$ are hydrogen, methyl or provided that when B$^1$ and B$^3$ are Q then B$^2$ is hydrogen or methyl and when B$^2$ is Q then B$^1$ and B$^3$ are hydrogen or methyl.

Illustrative examples of such compounds are 1,4-di(3,5-di-t-butyl-4-hydroxybenzyl)-2,3,5,6-tetramethylbenzene
1,3,5-tri(3,5-di-t-butyl-4-hydroxybenzyl)-2,4,6-trimethylbenzene 9. Phenolic compounds having the formula

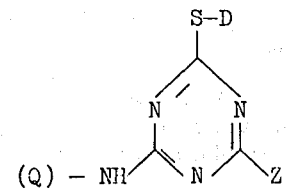

wherein
Z is NHQ, —S—D or —O—Q
D is alkyl group having from 6–12 carbon atoms or —(C$_x$H$_{2x}$)—S—R''

Illustrative examples of such compounds are 2,4-bis-(n-octylthio)-6-(3,5-di-t-butyl-4-hydroxyaniline)-1,3,5-triazine
6-(4-hydroxy-3-methyl-5-t-butylanilino)-2,4-bis-(n-octylthio-1,3,5-triazine
6-(4-hydroxy-3,5-dimethylanilino)-2,4-bis-(n-octylthio)-1,3,5-triazine
6-(4-hydroxy-3,5-di-t-butylanilino)-2,4-bis-(n-octylthio)-1,3,5-triazine.
6-(4-hydroxy-3,5-di-t-butylanilino)-4-(4-hydroxy-3,5-di-t-butylphenoxy)-2-(n-octylthio-1,3,5-triazine
2,4-bis(4-hydroxy-3,5-di-t-butylanilino)-6-(n-octylthio)-1,3,5-triazine.

10. Phenolic compounds having the formula

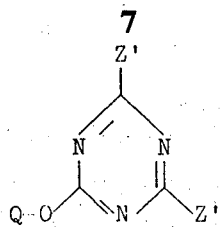

wherein Z' is —O—Q, —S—D or —S—(C$_{x'}$H$_{2x'}$)—SD

Illustrative examples of such compounds are 2,3-bis-(3,5-di-t-butyl-4-hydroxyphenoxy)-6-(n-octylthio)-1,3,5-triazine
2,4,6-tris-(4-hydroxy-3,5-di-t-butylphenoxy)-1,3,5-triazine.
6-(4-hydroxy-3,5-di-t-butylphenoxy)-2,4-bis-(n-octylthioethylthio)-1,3,5-triazine
6-(4-hydroxy-3-methylphenoxy)-2,4-bis-(n-octylthio)-1,3,5-triazine
6-(4-hydroxy-3-t-butylphenoxy)-2,4-bis-(n-octylthioethylthio)-1,3,5-triazine
6-(4-hydroxy-3-methyl-5-t-butylphenoxy)-2,4-bis-(n-octylthio)-1,3,5-triazine
2,4-bis-(4-hydroxy-3-methyl-5-t-butylphenoxy)-6-(n-octylthio)-1,3,5-triazine
2,4,6-tris-(4-hydroxy-3-methyl-5-t-butylphenoxy)-1,3,5-triazine
6-(4-hydroxy-3,5-di-t-butylphenoxy)-2,4-bis-(n-octylthiopropylthio)-1,3,5-triazine
6-(4-hydroxy-3,5-di-t-butylphenoxy)-2,4-bis-(n-dodecylthioethylthio)-1,3,5-triazine
2,4-bis-(4-hydroxy-3,5-di-t-butylphenoxy)-6-butylthio-1,3,5-triazine
2,4-bis-(4-hydroxy-3,5-di-t-butylphenoxy)-6-(n-octadecylthio)-1,3,5-triazine
2,4-bis-(4-hydroxy-3,5-di-t-butylphenoxy)-6-(n-dodecylthio)-1,3,5-triazine
2,4-bis-(4-hydroxy-3,5-di-t-butylphenoxy)-6-(n-octylthiopropylthio)-1,3,5-triazine
2,4-bis-(4-hydroxy-3,5-di-t-butylphenoxy)-6-(n-octylthioethylthio)-1,3,5-triazine
2,4-bis-(4-hydroxy-3,5-di-t-butylphenoxy)-6-(n-dodecylthioethylthio)-1,3,5-triazine.

11. Phenolic compounds having the formula

wherein p is an integer from 2 to 4 and R''' is a tetravalent radical selected from aliphatic hydrocarbons having from 1 to 30 carbon atoms
aliphatic mono and dithioethers having from 1 to 30 carbon atoms
aliphatic mono and diethers having from 1 to 30 carbon atoms
and z is an integer from 0 to 6.

Illustrative examples of such compounds are

Sub-class I n-Octadecyl 3-(3,5-di-t-butyl-4-hydroxyphenyl)-propionate
n-Octadecyl 2-(3,5-di-t-butyl-4-hydroxyphenyl)-acetate
n-Octadecyl 3,5-di-t-butyl-4-hydroxybenzoate
n-Hexyl 3,5-di-t-butyl-4-hydroxyphenylbenzoate
n-Dodecyl 3,5-di-t-butyl-4-hydroxyphenylbenzoate
Neo-dodecyl 3-(3,5-di-t-butyl-4-hydroxyphenyl)-propionate
Dodecyl β-(3,5-di-t-butyl-4-hydroxyphenyl)-propionate
Ethyl α-(4-hydroxy-3,5-di-t-butylphenyl)-isobutyrate
Octadecyl α-(4-hydroxy-3,5-di-t-butylphenyl)-isobutyrate
Octadecyl α-(4-hydroxy-3,5-di-t-butylphenyl)-propionate

Sub-class II 2-(n-octylthio)ethyl 3,5-di-t-butyl-4-hydroxybenzoate
2-(n-octylthio)ethyl 3,5-di-t-butyl-4-hydroxyphenylacetate
2-(n-octadecylthio)ethyl 3,5-di-t-butyl-4-hydroxyphenylacetate
2-(n-octadecylthio)ethyl 3,5-di-t-butyl-4-hydroxybenzoate
2-(2-hydroxyethylthio)ethyl 3,5-di-t-butyl-4-hydroxybenzoate
2,2'-thiodiethanol bis(3,5-di-t-butyl-4-hydroxyphenyl)acetate
Diethyl glycol bis-[3,5-di-t-butyl-4-hydroxyphenyl)-propionate]
2-(n-octadecylthio)ethyl 3-(3,5-di-t-butyl-4-hydroxyphenyl) propionate
2,2'-Thiodiethanol-bis-3-(3,5-di-t-butyl-4-hydroxyphenyl)propionate
Stearamido N,N-bis-[ethylene 3-(3,5-di-t-butyl-4-hydroxyphenyl)propionate]
n-Butylamino N,N-bis-[ethylene 3-(3,5-di-t-butyl-4-hydroxyphenyl)propionate]
2-(2-stearoyloxyethylthio)ethyl 3,5-di-t-butyl-4-hydroxybenzoate
2-(2-hydroxyethylthio)ethyl 7-(3-methyl-5-t-butyl-4-hydroxyphenyl)heptanoate
2-(2-stearoyloxyethylthio)ethyl 7-(3-methyl-5-t-butyl-4-hydroxyphenyl)heptanoate

Sub-class III 1,2-propylene glycol bis-[3-(3,5-di-t-butyl-4-hydroxyphenyl)propionate]
Ethylene glycol bis-[3-(3,5-di-t-butyl-4-hydroxyphenyl) propionate]
Neopentylglycol bis-[3-(3,5-di-t-butyl-4-hydroxyphenyl) propionate]
Ethylene glycol bis-(3,5-di-t-butyl-4-hydroxyphenylacetate)
Glycerine-1-n-octadecanoate-2,3-bis-(3,5-di-t-butyl-4-hydroxyphenylacetate
Pentaethylthritol-tetrakis-[3-(3,5-di-t-butyl-4-hydroxyphenyl)propionate]
1,1,1-trimethylol ethane-tris-3-(3,5-di-t-butyl-4-hydroxyphenyl)propionate
Sorbitol hexa-[3-(3,5-di-t-butyl-4-hydroxyphenyl)propionate]
1,2,3-butanetriol tris[3-(3,5-di-t-butyl-4-hydroxyphenyl)propionate]
2-hydroxyethyl 7-(3-methyl-5-t-butyl-4-hydroxyphenyl)heptanoate
2-stearoyloxyethyl 7-(3-methyl-5-t-butyl-4-hydroxyphenyl)heptanoate
1,6-n-hexanediol-bis[(3',5'-di-t-butyl-4-hydroxyphenyl)propionate]

12. Phenolic compounds having the formula $$Q-(CH_2)_x-\overset{\overset{O}{\uparrow}}{P}-OR''$$
$$\phantom{Q-(CH_2)_x-P-}OR''$$

where $x$ is an integer of 1 to 2.

Illustrative examples of such compounds are

Di-n-octadecyl 3,5-di-t-butyl-4-hydroxybenzylphosphonate
Di-n-octadecyl 3-t-butyl-4-hydroxy-5-methylbenzylphosphonate
Di-n-octadecyl 1-(3,5-di-t-butyl-4-hydroxyphenyl)-ethanephosphonate
Di-n-tetradecyl 3,5-di-t-butyl-4-hydroxybenzylphosphonate
Di-n-hexadecyl 3,5-di-t-butyl-4-hydroxybenzylphosphonate
Di-n-docosyl-3,5-di-t-butyl-4-hydroxybenzylphosphonate
Di-n-octadecyl 3,5-di-t-butyl-4-hydroxybenzylphosphonate 13. Phenolic compounds having the formula $$\begin{array}{c}(CH_2)WQ\\ \\O\diagup\!\!\!\!N\diagdown\!\!\!\!O\\ \\QW(H_2C)-N\diagdown\!\!\!\!\diagup N-(CH_2)WQ\\ \\O\end{array}$$

wherein W and Q are defined above.

Illustrative examples of such compounds are:

tris-(3,5-di-t-butyl-4-hydroxybenzyl)isocyanurate
tris-(3-t-butyl-4-hydroxy-5-methylbenzyl)isocyanurate The above phenolic hydrocarbon stabilizers are known and many are commercially available.

While any of the above mentioned antioxidants can be useful in combination with the ultraviolet light stabilizers of this invention, the preferred antioxidants consist of the hindered phenols in groups 1, 8, 9, 10, 11, 12 and 13 as mentioned above. The most preferred hindered phenols are those of groups 1, 9, 11, 12 and 13.

Further examples of antioxidants are those of the aminoaryl series for instance aniline and napthylamine derivatives as well as their heterocyclic derivatives such as:

phenyl-1-naphthylamine
phenyl-2-naphthylamine
N,N'-diphenyl-p-phenyldiamine
N,N'-di-sec.butyl-p-phenylenediamine
6-Ethoxy-2,2,4-trimethyl-1,2-dihydroquinoline
6-Dodecyl-2,2,4-trimethyl-1,2-dihydroquinoline
Mono- and di-octyliminodibenzyl and
polymerised 2,2,4-trimethyl-1,2-dihydroquinoline.

Ultraviolet absorbers and light protectants include
a. 2-(2'-hydroxyphenyl)benzotriazoles, for instance 5'-methyl; 3',5'-di-t-butyl; 5'-t-butyl; 5-chloro-3',- 5'-di-t-butyl; 5-chloro-3'-t-butyl-5'-methyl; 3'-sec.-butyl-5'-tert.butyl; 3'-[α-methylbenzyl]-5'-methyl-; 3'-[α-methylbenzyl]-5'-methyl-5-chloro-; 4'-octyl-; 3',5'-di-t-amyl; 3'-methyl-5'-carbomethoxyethyl; 5-chloro-3',5'-di-t-amyl derivatives.
b. 2,4-bis-(2'-hydroxyphenyl)-6-alkyl-S-triazines, for instance the 6-ethyl or 6-undecyl derivatives.
c. 2-hydroxybenzophenones, for instance the 4-hydroxy, 4-methoxy, 4-octoxy-, 4-decyloxy-, 4-dodecyloxy-, 4,2',4'-trihydroxy or 2'-hydroxy-4,4'-dimethoxy derivatives.
d. 1,3-Bis(2'-hydroxybenzoyl)-benzenes for instance, 1,3-bis-(2'-hydroxy-4'-hexyloxybenzoyl)benzene
1,3-bis-(2'-hydroxy-4'-octoxybenzoyl)benzene
1,3-bis-(2'-hydroxy-4'-dodecyloxybenzoyl)benzene
e. Aryl esters from optionally substituted benzoic acids such as phenylsalicylate, octylphenylsalicylate, dibenzoyl resorcinol, bis-(4-tert.butylbenzoyl) resorcinol, benzoylresorcinol and 3,5-di-tert.butyl-4-hydroxy-benzoic acid-2,4-di-tert.butyl phenyl ester and - octadecyl ester and -2-methyl-4,6-di-tert. butyl phenyl ester.
f. Acrylates, for instance α-Cyano-β,β-diphenylacrylic acid ethyl- or iso-octyl ester, α-carbomethoxycinnamic acid methyl- or butyl ester and N-(β-carbomethoxyvinyl)-2-methyl indoline.
g. Nickel compounds such as nickel complexes of 2,2'-thiobis-(4-tert. octylphenol), for instance the 1:1 and 1:2 complexes, optionally having other ligands such as n-butylamine, triethanolamine or N-cyclohexyl-diethanolamine; nickel complexes of bis-(4-tert. octylphenyl) sulphone such as the 2:1 complex, optionally having other ligands such as 2-ethylcaproic acid; nickel dibutyl dithiocarbamates; nickel salts of 4-hydroxy-3,5-di-tert.butyl-benzylphosphonic acid mono-alkyl esters such as the methyl-, ethyl- or butyl esters; the nickel complex of 2-hydroxy-4-methyl-phenyl-undecylketonoxime; and nickel-3,5-di-tert.butyl-4-hydroxy benzoate, and
h. Oxalic acid diamides, for instance
4,4'-dioctyloxyoxanilide
2,2'-dioctyloxy:5,5'-di-tert.butyl-oxanilide
2,2'-di-dodecyloxy-5,5'-di-tert.butyl oxanilide
2-ethoxy-5-tertiarybutyl-2'-ethyl-oxanilide
2-ethoxy-2'-ethyl-oxanilide
mixtures of o- and p- methoxy and ethoxy- di-substituted oxanilides and the compound of formula:

$$\begin{array}{c}CH_3\diagdown\phantom{xxxxxxxxxxxxxxxxx}\diagup CH_3\\ N-(CH_2)_3-NHCOCONH(CH_2)_3N\\ CH_3\diagup\phantom{xxxxxxxxxxxxxxxxx}\diagdown CH_3\end{array}$$

Phosphite stabilisers include triphenyl phosphite, diphenylalkyl, phosphites, phenyl dialkyl phosphites, trinonylphenyl phosphite, trilauryl phosphite, trioctadecyl phosphite, 3,9-di-isodecyloxy-2,4,8,10-tetraoxa- 3,9-diphosphaspiro-(5,5)-undecane and tri-(4-hydroxy-3,5-di-tert.butylphenyl)phosphite.

Peroxide-decamposing compounds for polyolefins include esters of β-thiodipropionic acids, for instance the lauryl-, stearyl-, myristyl- or tridecyl esters, salts of mercaptobenzimidazoles such as the zinc salt and diphenylthiourea.

Suitable polyamide stabilisers include copper salts in combination with iodides and/or further phosphorus compounds and salts of bivalent manganese.

Basic co-stabilisers are, for example, polyvinylpyrrolidone, melamine, benzoguanamine, triallyl cyanurate, dicyandiamide; urea derivatives, hydrazine derivatives, amines, polyamides, polyurethanes, alkali and alkaline earth salts of higher saturated or unsaturated fatty acids such as calcium stearate.

Polyvinyl chloride stabilisers include organotin compounds, organo lead compounds and Ba/Cd salts of fatty acids.

Examples of nucleation agents are 4-tert.butyl benzoic acid, adipic acid and diphenylacetic acid.

As with the compound of formula I, any further additive is advantageously employed in a proportion within the range of from 0.01% to 5% by weight, based on the weight of untreated polymeric material.

In binary combinations with one or more antioxidants listed above or in tertiary combinations with such antioxidants and U.V. absorbers listed above, the compounds of formula I provide very effective stabiliser packages in polyolefine formulations.

Many of the compounds of formula I are novel, and where these compounds are new, they form part of the present invention.

Accordingly, the present invention also provides compounds having the formula:

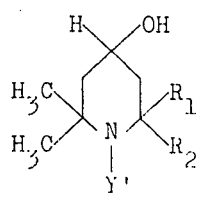
II wherein $R_1$ and $R_2$ have their previous significance and $Y'$ is a straight- or branched alkyl residue having from 5 to 20 carbon atoms, an alkenyl or alkynyl residue having from 3 to 20 carbon atoms, an aralkyl residue having from 7 to 12 carbon atoms, or the group $-CH_2X'$ wherein $X'$ is the group

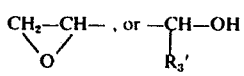

wherein $R_3 1$ is hydrogen or a methyl residue, or $X^1$ is the group

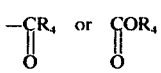

wherein $R_4$ has its previous significance.

The preferences previously expressed for substituents Y of compounds of formula I apply equally, within the limits of the restricted definition, to substituent $Y^1$ of the compounds of formula II.

The present invention also provides a first process of producing a compound of formula II comprising reacting a piperidinol having the formula:

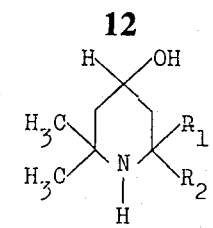
III wherein $R_1$ and $R_2$ have their previous significance with a compound IV capable of replacing the hydrogen atom on the nitrogen atom of the compound of formula III by the substituent $Y^1$.

Thus, to produce by this process a compound of formula II in which $Y^1$ is an alkyl, alkenyl, alkynyl or aralkyl residue, the compound of formula III is reacted with a compound IV which is an alkylating, alkenylating, alkynylating or arakylating agent. Preferably, the compound IV in this case is an alkyl, alkenyl, alkynyl or aralkyl halide.

To produce a compound of formula II wherein $Y^1$ is alkyl or arakyl Compound IV may also be the aldehyde or ketone corresponding to the substituent $Y^1$, together with formic acid under Leuckart reaction conditions.

Similarly, to produce a compound of formula II wherein $Y^1$ is a substituent $-CH_2X^1$ wherein $X^1$ is

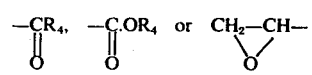

the compound of formula III may be reacted with a compound having the formula:

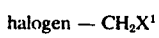
V wherein $X^1$ has its previous significance.

The reaction is conveniently effected by heating compounds III and V together in the presence of an acid-binding agent which may be an excess of the compound of formula III or another base, for instance trietylamine.

To introduce a substituent $Y^1$ wherein $Y^1$ is $-CH_2X^1$ and $X^1$ is a residue

the compound of formula III may be reacted with an olefine oxide having the formula:

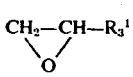
VI wherein $R_3 1$ has its previous significance.

The present invention further provides a second process of producing a compound of formula I comprising hydrogenating or reducing a compound having the formula:

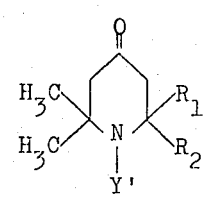
VII wherein $R_1$, $R_2$ and $Y^1$ have their previous significance, with the proviso that $Y^1$ is not an unsaturated residue.

When this process is effected by an hydrogenation technique, the reaction is preferably effected in the presence of a metal hydrogenation catalyst and in the presence of an organic solvent inert under the reaction conditions. Suitable metal hydrogenation catalyst include platinum, palladium, ruthenium, rhodium and Raney nickel, optionally supported on an inert carrier such as calcium carbonate or carbon black. Examples of inert solvents for use in the hydrogenation reaction include toluene and cyclohexane.

When the reaction is effected by chemical reduction, suitable reducing agents include metal hydrides such as $LiAlH_4$, $NaBH_4$ or secondary alcohols in the presence of a catalyst, e.g. aluminium isopropoxide, for example a Meerwein Ponndorof-Varley reduction.

Many of the starting materials of formula VII are new compounds. They may be prepared for instance, by any of the following methods.

Firstly, the compounds VII may be prepared by reacting the corresponding >NH compound having the formula:

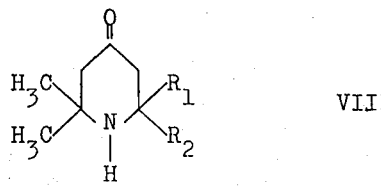

VIII with a compound capable of replacing the hydrogen atom on the nitrogen atom by the group $Y^1$. In modifications of this reaction, the compound VIII may be replaced by derivatives thereof, for instance by a ketal derived from a compound of formula VIII.

The compounds of formula VIII are known compounds and may, in turn, be prepared by methods well-known per se.

According to a third, less preferred, process there is provided a process of producing a compound of formula II, comprising hydrolyzing an O-substituted derivative having the formula:

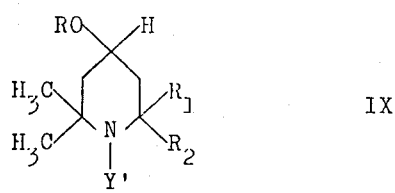

IX wherein $R_1$, $R_2$ and $Y^1$ have their previous significance and R is an alkyl residue optionally substituted having from 1 to 20 carbon atoms, a cycloalkyl residue having from 5 to 12 carbon atoms, an alkenyl or alkynyl residue having from 3 to 20 carbon atoms, an acyl residue having from 1 to 20 carbon atoms or a carbamoyl or thiocarbamoyl residue having from 1 to 20 carbon atoms.

The hydrolysis reaction may be carried out, for example, by contacting the compound of formula IX with an aqueous acidic or alkaline medium, preferably at an elevated temperature.

Examples of compounds of formula IX which may be used in the third process according to the invention include 1-(2'-hydroxyethyl)-4-butoxy-2,2,6,6-tetramethylpiperidine, 1-n-propyl-2,2,6,6-tetramethylpiperidine-4-octanoate and 1-n-butyl-2,2,6,6-tetramethylpiperidine-4-benzoate.

Some Examples will now be given. Parts and percentages are by weight unless otherwise stated.

EXAMPLE 1

A mixture of 15.7 parts of 2,2,6,6-tetramethylpiperidin-4-ol and 12.5 parts of n-dodecyl bromide in 50 parts of ethyl alcohol was heated under reflux conditions for 72 hours. The cooled reaction mixture was filtered to remove 2,2,6,6-tetramethylpiperidin-4-ol hydrobromide formed during the reaction and the ethyl alcohol solvent was removed by distillation under reduced pressure. The residue was treated with petroleum under (b.p. 40°–60°C) and filtered to remove the unreacted 2,2,6,6-tetramethylpiperidin-4-ol and the petroleum ether solvent was removed by distillation under reduced pressure. Fractional distillation of the residue gave 1-n-dodecyl-2,2,6,6-tetramethylpiperidin-4-ol having a melting point of 41°–2°C and the following elemental analysis by weight:

|  | FOUND | REQUIRED (for $C_{21}H_{43}NO$) |
|---|---|---|
| CARBON | 77.75% | 77.47% |
| HYDROGEN | 12.74% | 13.31% |
| NITROGEN | 3.96% | 4.30% |

EXAMPLE 2

A mixture of 31.4 parts of 2,2,6,6-tetramethylpiperidin-4-ol and 17.1 parts of benzyl bromide in 125 parts of ethyl alcohol was heated under reflux conditions for 96 hours. The cooled reaction mixture was filtered to remove 2,2,6,6-tetramethylpiperidin-4-ol hydrobromide formed during the reaction and the ethyl alcohol solvent was removed by distillation under reduced pressure. Purification of the residue by chromatography on a aluminia column using chloroform as the solvent gave 1-benzyl-2,2,6,6-tetramethylpiperidin-4-ol having a melting point of 151°–2°C and the following elemental analysis by weight

|  | FOUND | REQUIRED (for $C_{16}H_{25}NO$) |
|---|---|---|
| CARBON | 77.90% | 77.68% |
| HYDROGEN | 10.15% | 10.19% |
| NITROGEN | 5.38% | 5.66% |

EXAMPLE 3

A mixture of 78.5 parts of 2,2,6,6-tetramethylpiperidine-4-ol and 30.25 parts of allyl bromide in 250 parts of ethyl alcohol was heated under reflux conditions for 48 hours. The cooled reaction mixture was filtered to remove 2,2,6,6-tetramethylpiperidin-4-ol hydrobromide formed during the reaction and the ethyl alcohol solvent was removed by distillation under reduced pressure. The residue was triturated with cold petroleum ether (b.p. 40°–60°C) to remove a small amount of unreacted 2,2,6,6-tetramethylpiperidin-4-ol. Crystallisation of the residue from 40°–60°C petroleum ether gave 1-allyl-2,2,6,6-tetramethylpiperidin-4-ol having a melting point of 84°–5°C and the following elemental analysis by weight.

|  | FOUND | REQUIRED (for $C_{12}H_{25}NO$) |
|---|---|---|
| CARBON | 73.18% | 73.04% |
| HYDROGEN | 11.61% | 11.75% |
| NITROGEN | 6.79% | 7.10% |

EXAMPLE 4

A mixture of 3.14 parts of 2,2,6,6-tetramethylpiperidin-4-ol, 10 parts of propylene oxide and 10 parts of isopropanol was charged to an autoclave. A pressure of 100 atmospheres of nitrogen was applied and the mixture heated at 160°C for 6 hours. The isopropanol solvent and unreacted propylene oxide were removed by distillation under reduced pressure. Crystallisation of the residue from cyclohexane gave 3.0 parts of 1[2-hydroxypropyl]-2,2,6,6-tetramethylpiperidin-4-ol having a melting point of 97°–8°C and on further purification of 107°–8°C and the following elemental analysis by weight:

|  | Found | Required (for $C_{12}H_{25}NO_2$) |
|---|---|---|
| Carbon | 67.04% | 66.93% |
| Hydrogen | 11.66% | 11.70% |
| Nitrogen | 6.32% | 6.50% |

EXAMPLE 5

A mixture of 3.14 parts of 2,2,6,6-tetramethylpiperidin-4-ol, 5 parts of ethylene oxide and 10 parts of isopropanol was charged to a previously cooled autoclave. A pressure of 100 atmospheres of nitrogen was applied and the mixture heated a 160°C for 6 hours.

The isopropanol solvent was removed by distillation under reduced pressure. Crystallisation of the residue from toluene gave 1.1 parts of 1-[2-hydroxyethyl]-2,2,6,6-tetramethylpiperidin-4-ol having a melting point of 182°C and the following elemental analysis by weight:

|  | Found | Required (for $C_{11}H_{23}NO_2$) |
|---|---|---|
| Carbon | 65.90% | 65.63% |
| Hydrogen | 11.52% | 11.52% |
| Nitrogen | 6.72% | 6.96% |

EXAMPLE 6

38 Parts of polypropylene were homogenised with 0.076 part of n-octadecyl-β-(4'-hydroxy-3',5'-di-t-butylphenyl)propionate in a kneading machine at a temperature of 200°C over a period of 3 minutes. 0.19 part of 1,2,2,6,6-pentamethylpiperidin-4-ol was then added and homogenisation continued for another 7 minutes.

The homogenised mixture was removed from the kneader and pressed to a thickness of from 2 to 3 mm. in a press at a temperature of 200°C. 9 Parts of the polypropylene mixture were then charged into a press in which the press-plates were protected by 0.1 mm thick aluminium foil. The sample was surrounded by four strips of steel skim, 0.3 mm thick, in the form of a square, acting as spacers between the aluminium foils. The press was closed and for 2 minutes no pressure was applied. The pressure was then increased over 2 minutes up to a maximum of 12 tons and this pressure held for a further 2 minutes, the temperature being 260°C. The pressure was released and the material (0.3 mm thick) was cooled immediately under running water.

2.2 parts of this material was cut in the form of a square and recharged to the press. Conditions were as for the previous pressure except that 0.1 mm thick steel skim was used for spacing between the aluminium foils. The press was closed and no pressure was applied for 2 minutes. Over another 2 minutes the pressure was increased to 8 tons, the press temperature being 260°C. This pressure was maintain for 2 minutes and then the pressure released. The "sandwich" of the 0.1 mm thick polypropylene foil and the aluminium foils was then removed and tempered immediately for 1 hour in a circulating-air oven maintained at 150°C. The "sandwich" was then quenched in running cold water and the aluminium foils were peeled from the inner polypropylene foil and the skin spacers removed.

A section measuring 44 × 100 mm was separated from the 0.1 mm tempered polypropylene foil and exposed to light irradiation in a fademeter device consisting of a circular bank of 28 alternate sunlight and blacklight lamps. The sunlight lamps were 2 feet long, 20-watt fluorescent lamps characterised by a peak emission of 3000 Angstrom units; the blacklight lamps were 2 feet long, 20-watt ultraviolet lamps characterised by a peak emission of 3500 Angstrom units. The sample was rotated concentrically within the bank of lamps so that the radiation therefore was uniformly distributed over the section under test.

The exposed sample was examined periodically and the time (T) at which the sample reached 50% of the initial elongation at break was noted.

The time (Tc) for the elongation of a control sample (not containing the product of Example 1) to decrease to 50% of the initial elongation was then determined.

The performance of the compound of formula I as a light stabiliser could then be assessed by determining the factor T/Tc.

The results obtained including those relating to other compounds of formula I are summarised in the following Table.

Table

| Example | Additive | Time (T) to 50% initial elongation at break (hours) | Factor i.e. T additive / T control |
|---|---|---|---|
| — | none (control) | 190 | 1 |
| — | 2-(2'-hydroxy-3',5'-di-t-butylphenyl)-5-chlorobenzotriazole | 500 | 2.6 |
| 6 | 1,2,2,6,6-pentamethyl-piperidin-4-ol | 890 | 4.7 |

EXAMPLE 7

A mixture of 15.7 parts of 2,2,6,6-tetramethylpiperidin-4-ol and 6.85 parts of epibromohydrin in 50 parts of ethyl alcohol was heated for 24 hours. The cooled reaction mixture was filtered to remove 2,2,6,6-tetramethylpiperidin-4-ol hydrobromide and the solvent removed by distillation in vacuo. The resultant material was dissolved with heating in petroleum ether (of boiling range 100°–120°C) and the immediate crop of crystals of 2,2,6,6-tetramethylpiperidine-4-ol removed. Evaporation afforded 2-(2′,3′-epoxy-n-propyl)-2,2,6,6-tetramethylpiperidin-4-ol as a colourless solid of melting point 49°–53°C. This material gave the following elemental analysis by weight.

|  | Required for $C_{12}H_{23}NO_2 \cdot CH_3CH_2OH$ |  |
|---|---|---|
| Carbon | 64.87% | 64.83% |
| Hydrogen | 10.87% | 11.27% |
| Nitrogen | 5.99% | 5.40% |

EXAMPLE 8

A mixture of 15.7 parts of 2,2,6,6-tetramethylpiperidin-4-ol and 8.3 parts of ethyl bromoacetate in 50 parts of ethyl alcohol was heated at reflux for 48 hours. The cooled reaction mixture was filtered to remove 2,2,6,6-tetramethylpiperidin-4-ol hydrobromide and the solvent removed by distillation in vacuo. The residue was triturated with 40°–60°C petroleum ether to remove the unreacted 2,2,6,6-tetramethylpiperidin-4-ol. The filtrate was then distilled under reduced pressure to yield pure 1-ethoxy-carbonylmethyl-2,2,6,6-tetramethylpiperidin-4-ol as a colourless liquid (of boiling point 116°C at 0.2 mm) which slowly solidified on standing (melting point 42°–42.5°C). This material gave the following elemental analysis by weight:

|  | Found | Required for $C_{13}H_{25}NO_3$ |
|---|---|---|
| Carbon | 64.27% | 64.16% |
| Hydrogen | 10.30% | 10.36% |
| Nitrogen | 5.57% | 5.76% |

EXAMPLE 9

1-[2-hydroxy-2-phenylethyl]-2,2,6,6-tetramethyl-piperidin-4-ol

A mixture of 3.14 parts of 2,2,6,6-tetramethylpiperidin-4-ol, 30 parts of styrene oxide and 30 parts of n-hexanol was heated at reflux for 18 hours. The n-hexanol solvent and unreacted styrene oxide were removed by distillation under reduced pressure. Crystallisation of the residue from cyclohexane gave 4.2 parts of 1-[2-hydroxy-2-phenylethyl]-2,2,6,6-tetramethyl-piperidin-4-ol having a melting point of 123°C and the following elemental analysis by weight.

|  | Found | Required (for $C_{17}H_{27}NO_2$) |
|---|---|---|
| Carbon | 73.87 | 73.61 |
| Hydrogen | 9.87 | 9.81 |
| Nitrogen | 5.22 | 5.05 |

We claim:
1. A compound of the formula

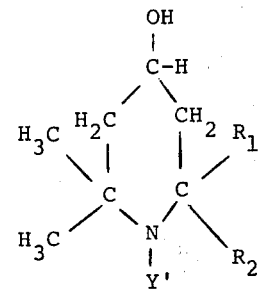

wherein $R_1$ and $R_2$ are the same or different and each is a straight- or branched alkyl residue having from 1 to 12 carbon atoms, or $R_1$ and $R_2$, together with the carbon atom to which they are attached, form a cycloalkyl residue having from 5 to 12 carbon atoms, or the group:

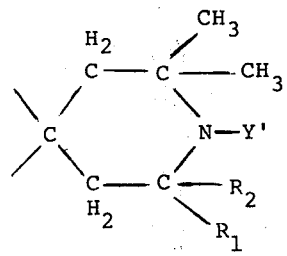

wherein $R_1$ and $R_2$ are as defined above and Y′ is a straight- or branched alkyl having from 5 to 20 carbon atoms, an alkenyl or alkynyl having from 3 to 20 carbon atoms, an aralkyl selected from benzyl, α-methylbenzyl, p-methyl- α-methylbenzyl and α-naphthylmethyl or the group —CH₂X′ wherein X′ is the group

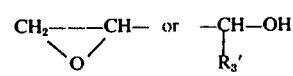

wherein $R_3′$ is hydrogen or a methyl residue, or X is the group

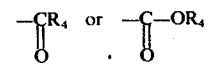

wherein $R_4$ is alkyl residue having from 1 to 20 carbon atoms.

2. A compound according to claim 1 wherein $R_1$ and $R_2$ are each methyl.

3. A compound according to claim 1 wherein Y′ is an alkyl having from 5 to 20 carbon atoms, an alkenyl or alkynyl having 3 or 4 carbon atoms, an aralkyl having from 7 to 11 carbon atoms selected from benzyl, α-methylbenzyl, p-methyl- α-methylbenzyl and α-naphthylmethyl, a hydroxyethyl or 2-hydroxypropyl.

4. A compound according to claim 1 which is 1-n-dodecyl-2,2,6,6-tetramethylpiperidin-4-ol.

5. A compound according to claim 1 which is 1-benzyl-2,2,6,6-tetramethylpiperidin-4-ol.

6. A compound according to claim 1 which is 1-allyl-2,2,6,6-tetramethylpiperidin-4-ol.

7. A compound according to claim 1 which is 1-(2-hydroxypropyl)-2,2,6,6-tetramethylpiperidin-4-ol.

* * * * *